(12) United States Patent
Eliu et al.

(10) Patent No.: US 6,274,761 B1
(45) Date of Patent: Aug. 14, 2001

(54) PROCESS FOR THE PREPARATION OF SULPHONATED DISTYRYL-BIPHENYL COMPOUNDS

(75) Inventors: Victor Paul Eliu, Lörrach; Julia Völkel, Grenzach-Wyhlen, both of (DE); Peter Rohringer, Schönenbuch (CH); Roger Wolfgang Basler, Binzen; Brigitte Gerhild Sereinig, Grenzach-Wyhlen, both of (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/646,397
(22) PCT Filed: Mar. 16, 1999
(86) PCT No.: PCT/EP99/01695
 § 371 Date: Sep. 15, 2000
 § 102(e) Date: Sep. 15, 2000
(87) PCT Pub. No.: WO99/47495
 PCT Pub. Date: Sep. 23, 1999

(30) Foreign Application Priority Data

Mar. 19, 1998 (EP) .................................. 98810232

(51) Int. Cl.$^7$ ................................. C07C 303/00
(52) U.S. Cl. .................. 562/87; 562/405; 585/435; 585/657
(58) Field of Search .......... 562/87, 405; 585/435, 585/657

(56) References Cited

U.S. PATENT DOCUMENTS

| | | | |
|---|---|---|---|
| 3,984,399 | 10/1976 | Weber et al. | 260/240 |
| 4,115,436 | 9/1978 | Katsuragawa et al. | 260/505 |
| 4,925,595 | 5/1990 | Hefti et al. | 252/301.21 |
| 5,145,991 | * 9/1992 | Weber et al. | 562/87 |

FOREIGN PATENT DOCUMENTS

| | | |
|---|---|---|
| 594 617 | 1/1978 | (CH) . |
| 1 794 386 | 11/1973 | (DE) . |
| 28 08 927 | 9/1979 | (DE) . |
| 0 298 361 | 1/1989 | (EP) . |
| 0 325 975 | 8/1989 | (EP) . |
| 2 168 210 | 8/1973 | (FR) . |
| 1247934 | 9/1971 | (GB) . |
| 2168210 | * 8/1973 | (WO) . |

OTHER PUBLICATIONS

Chemical Abstracts, vol. 98, (1983) No. 6, 98:35526b of JP 57/123, 262.

* cited by examiner

Primary Examiner—Ralph Gitomer
Assistant Examiner—D Khare
(74) Attorney, Agent, or Firm—Kevin T. Mansfield

(57) ABSTRACT

A process for the preparation of sulphonated distyryl-biphenyl compounds of formula (1), in which $R_1$ and $R_2$, independently, are hydrogen, $C_1$–$C_5$-alkyl, $C_1$–$C_5$-alkyl or halogen, and M represents Li, K, an alkaline earth metal or ammonium, characterized by, firstly, reacting a compound of formula (2) with a di- or trialkylamine containing 6–12 carbon atoms in each alkyl group, in a two-phase system consisting of strong aqueous mineral acid and a water immisicible organic solvent and, secondly, reacting the resulting lypophilic ammonium salt with LiOH, KOH, an alkaline earth metal hydroxide, ammonia, a mono-, di- or trialkylamine or a tetraalkylammonium hydroxide, all containing 1–4 carbon atoms in each alkyl group; mono-, di- or tri($C_2$–$C_4$)alkanolamine, morpholine, piperdine or pyrrolidine.

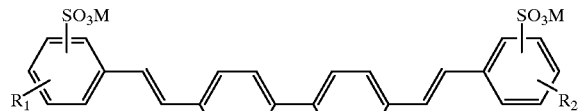

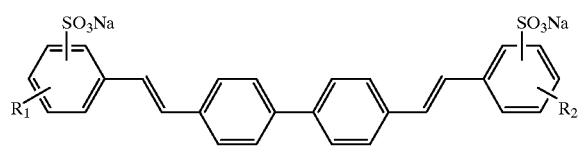

11 Claims, No Drawings

PROCESS FOR THE PREPARATION OF SULPHONATED DISTYRYL-BIPHENYL COMPOUNDS

The present invention relates to a new process for the preparation of salts of sulphonated distyryl-biphenyl compounds.

Distyryl-biphenyl sulphonic acid salts, their preparation and use as optical brightening agents have been described, for example in British Patent Specification 1,247,934 and in French Patent Specification 2,168,210. However, due to the method of synthesis of these compounds, the resulting bis-stilbene sulphonic acids are produced in the form of their sodium salts. Despite the inherent fluorescence of these systems, which render them useful as optical brightening agents, such sodium salts may also be disadvantageous with regard to properties such as water solubility and colouration. Hence, a simple method for the interconversion of such sodium salts into those possessing more desirable properties would be advantageous.

Methods for the interconversion of such salts are, for example, by way of the free acid, whereby the free acid must be far more insoluble than the sodium salt and also readily filterable, which, in general, is not the case with such bis-stilbene sulphonic acids. The free acid may also be converted into other salts by the use of a solid ion exchange resin, but, in the case, the free acid must be readily water soluble, which again is not the case with such compounds. Direct ion exchange can only be performed in order to convert a readily soluble salt into a far less soluble derivative, which is not a requirement in the present case.

Surprisingly, by way of ion pair extraction, a process has now been found for the preparation of salts of sulphonated distyryl-biphenyl compounds of formula:

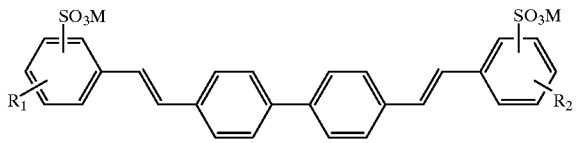

(1)

in which $R_1$ and $R_2$, independently, are hydrogen, $C_1$–$C_5$-alkyl, $C_1$–$C_5$-alkoxy or halogen, and M represents Li, K, an alkaline earth metal, ammonium, a mono-, di- or trialkylammonium or a tetraalkylammonium, all containing 1–4 carbon atoms in each alkyl group; a mono-, di- or tri ($C_2$–$C_4$)alkanolammonium, morpholinium, piperidinium or pyrrolidinium by, firstly, reacting a compound of formula:

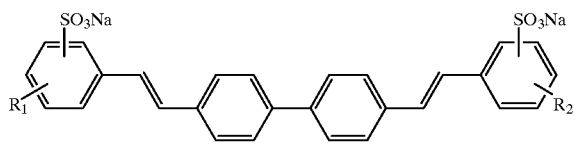

(2)

with a di- or trialkylamine containing 6–12 carbon atoms in each alkyl group, in a two-phase system consisting of strong aqueous mineral acid and a water immiscible organic solvent and, secondly, reacting the resulting lypophilic ammonium salt with LiOH, KOH, an alkaline earth metal hydroxide, ammonia, a mono-, di- or trialkylamine or a tetraalkylammonium hydroxide, all containing 1–4 carbon atoms in each alkyl group; a mono-, di- or tri($C_2$–$C_4$) alkanolamine, morpholine, piperidine or pyrrolidine.

When, in formula (1), $R_1$ and $R_2$ represent $C_1$–$C_5$-alkyl, these may be methyl, ethyl, n- or isopropyl, n-, sec-,or t-butyl, n-pentyl, iso-amyl or sec-amyl groups. When, in formula (1), $R_1$ and $R_2$ represent $C_1$–$C_5$-alkoxy, these may be methoxy, ethoxy, n- or isopropoxy, n-, sec-,or t-butoxy, n-pentyloxy, iso-amyloxy or sec-amyloxy groups. When, in formula (1), $R_1$ and $R_2$ represent halogen, these may be fluorine, chlorine, bromine, or iodine, preferably chlorine.

When M represents an alkaline earth metal these are preferably Ca or Mg, whilst when M represents ammonium these may be $NH_4$, mono-, di-, tri- or tetramethylammonium, mono-, di-, tri- or tetraethylammonium, mono, di-, tri- or tetra-n- or isopropylammonium, mono, di-, tri- or tetra-n-, sec- or t-butylammonium, mono-, di- or triethanolammonium, mono-, di- or tri-n- or isopropanolammonium, mono-, di- or tri-n- sec- or t-butanolammonium, morpholinium, piperidinium or pyrrolidinium.

As di- or trialkylamines containing 6–12 carbon atoms in each alkyl group, utilised in the first reaction step, these may be any of the isomers of di- or trihexylamine, di or triheptylamine, di- or trioctylamine, di- or trinonylamine, di- or tridecylamine, di- or triundecylamine or di- or tridodecylamine, but are preferably tri-n-octylamine or tri-isooctylamine.

The process of the present invention is particularly useful for the preparation of compounds of formula (1), whereby, $R_1$ and $R_2$ both represent hydrogen, $C_1$–$C_3$-alkyl, $C_1$–$C_3$-alkoxy, bromine or chlorine, and M represents Li, K, Mg, Ca or an ammonium group.

The process of the present invention is preferably used for the preparation of compounds of formula (1) in which $R_1$ and $R_2$ both represent hydrogen and M represents Li, K, Mg, Ca, —$N(R_3)_4$, whereby $R_3$ represents hydrogen or $C_1$–$C_4$-alkyl, all $R_3$ groups not necessarily being identical, or $C_2$–$C_4$alkanolammonium.

The process of the present invention is most particularly useful for the preparation of compounds of the formula

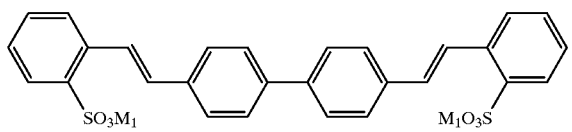

(3)

whereby $M_1$ represents Li, K, —$N(R_3)_4$, where $R_3$, represents hydrogen, $C_1$–$C_4$-alkyl, or $C_2$–$C_4$-alkanol and also for the preparation of compounds of formula

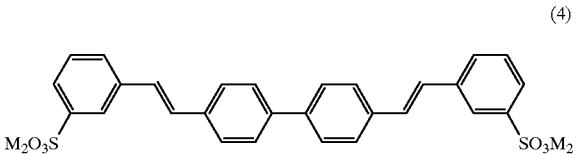

(4)

whereby $M_2$ represents Li, K or —$N(n-C_4H_9)_4$.

The molar ratios of these amines to that of compound (2) lies in the range of from about 2 to about 4, preferably being in the range of 2.2 to 4.

Any strong mineral acid may be utilised in the initial reaction step, specific examples being hydrochloric acid, phosphoric acid or, in particular, sulphuric acid, the amount used being such that the pH of the aqueous layer lies within the range of from 1 to 5, especially within the range of from 2 to 3.

The water immiscible organic solvent utilised in the first reaction step may be a substituted or unsubstituted benzene, alkane or cycloalkylene, or mixtures thereof, specific examples of such being benzene, toluene, mono- or dichlorobenzenes, nitrobenzene, anisole, xylenes, pentane, hexane, cyclopentane or cyclohexane, isomeric mixtures of xylenes being especially preferred.

The temperature at which the initial reaction step is carried out may lie within the range of from about 10 to about 90° C., preferably between 50 and 80° C.

In dissolved or finely divided states, the brighteners obtained by the above process display a more or less pronounced fluorescence. They are therefore used, according to the invention, for optically brightening synthetic or natural organic materials.

Examples of such materials which may be mentioned, without the review given below being intended to express any limitabon thereto, are textile fibres from the following groups of organic materials, insofar as optical brightening thereof enters into consideration:

(a) Polyamides which are obtainable as polymerisation products by ring opening, for example those of the polycaprolactam type, (b) polyamides which are obtainable as polycondensation products based on bifunctional or polyfunctional compounds capable of undergoing a condensation reaction, such as hexamethylenediamine adipate and (c) natural textile organic materials of animal or vegetable origin, for example based on cellulose or proteins, such as cotton or wool, linen or silk.

The organic materials to be optically brightened can be in diverse stages of processing and are preferably finished textile products. They can, for example be in the form of hank goods, textile filaments, yarns, twisted yarns, nonwovens, felts, textile fabrics, textile composites or knitted fabrics.

The brighteners defined above are of particular importance for the treatment of textile fabrics. The treatment of textile substrates is advantageously carried out in an aqueous medium in which the particular optical brighteners are present in a finely divided form (suspensions, so-called microdispersions and in some cases solutions). Dispersing agents, stabilisers, wetting agents and further auxiliaries can optionally be added during the treatment.

The treatment is usually carried out at temperatures of from about 20° to 140° C., for example at the boiling point of the bath, or in the region thereof (about 90° C.). For the finishing, according to the invention, of textile substrates it is also possible to use solutions or emulsions in organic solvents, as are used in dyeing practice in so-called solvent dyeing (pad-thermofix method and the exhaustion dyeing process in dyeing machines).

The optical brighteners which can be used according to the present invention can also be employed, for example, in the following use forms:

(a) In mixtures with so-called "carriers", wetting agents, softeners, swelling agents, antioxidants, light stabilisers, heat stabilisers and chemical bleaching agents (chlorite bleach and bleaching bath additives).

(b) In mixtures with crosslinking agents and finishing agents (for example starch or synthetic finishing agents) and also in combination with very diverse textile finishing processes, especially synthetic resin finishes (for example crease resistant finishes such as "wash-and-wear", "permanent press" and "no-iron"), and also flame resistant finishes, soft handle finishes, anti-soiling finshes or anti-static finishes or antimicrobial finishes.

(c) As additives to various soaps and washing agents.

(d) In combination with other substances having an optical brightening action.

If the brightening process is combined with textile treatment or finishing methods, the combined treatment can in many cases advantageously be effected with the aid of corresponding stable formulations which contain the compounds having an optical brightening action in a concentration such that the desired brightening effect is obtained.

In certain cases, the full effect of the brightener is achieved by an after-treatment. This can be, for example, a chemical treatment (for example acid treatment), a thermal treatment (for example heat) or a combined chemical/heat treatment.

The amount of the optical brighteners to be used according to the invention, relative to the material to be optically brightened, can vary within wide limits. A distinct and durable effect can already be achieved with vary small amounts and in certain cases, for example, with amounts of 0.03% by weight. However amounts of up to about 0.5% by weight can also be used. For most cases of interest in practice, amounts of between 0.05 and 0.5% by weight relative to the material to be brightened, are preferably of interest.

The optical brighteners are also especially suitable as additives for washing baths or to industrial and household washing agents and they can be added in various ways. They are appropriately added to washing baths in the form of their solutions in water or organic solvents or also in a state of fine division as aqueous dispersions or slurries. They, or their components, are advantageously added to household or industrial washing agents at any phase of the manufacturing process of the washing agent, for example to the so-called "slurry" prior to spray-rying of the washing powder or during the preparation of liquid washing agent combinations. The compounds can be added both in the form of a solution or dispersion in water or other solvents and also without auxiliaries in the form of a dry brightener powder. However, they can also be sprayed, in the dissolved or pre-dispersed form, onto the finished washing agent.

Washing agents which can be used are the known mixtures of detergent substances, such as, for example, soap in the form of chips and powders, synthetic products, soluble salts of sulphonic acid half-esters of higher fatty alcohols, arylsulphonic acids, which are substituted by higher alkyl and/or polysubstituted by alkyl, carboxylic acid esters with alcohols of medium to higher molecular weight, fatty acid acylaminoalkyl- or aminoaryl-glycerol-sulphonates, phosphoric acid esters of fatty alcohols and the like. So-called "builders" which can be used are, for example, alkali metal polyphosphates and alkali metal polymeta-phosphates, alkali metal pyrophosphates, alkali metal salts of carboxyethylcellulose and other "soil redeposition inhibitors", and also alkali metal silicates, alkali metal carbonates, alkali metal borates, alkali metal perborates, nitrilotriacetic acid, ethylenediamine-tetraacetic acid and foam stabilisers, such as alkanolamides of higher fatty acids. Furthermore, the washing agents can contain, for example: antistatic agents, superfatting skin protection agents, such as lanolin, enzymes, antimicrobial agents, perfumes and dyestuffs.

The brighteners have the particular advantage that they are also effective in the presence of active chlorine donors, such as, for example, hypochlorite and can be used without substantial loss of the effects in washing baths with non-ionic washing agents, for example alkylphenol polyglycol ethers. Also in the presence of perborate or peracids and activators, for example tetraacetylglycoluril or ethylenediamine-tetraacetic acid are the new brighteners very stable both in pulverulent washing agent and in washing baths.

The brighteners according to the invention are added in amounts of 0.005 to 2% or more and preferably of 0.03 to 0.5%, relative to the weight of the liquid or pulverent ready-to-use washing agent. When they are used to wash textiles made of cellulose fibres, polyamide fibres, cellulose fibres with a high grade finish, wool and the like, wash liquors which contain the indicated amounts of the optical brighteners according to the invention impart a brilliant appearance in daylight.

The washing treatment is carried out, for example, as follows: The indicated textiles are treated for 1 to 30 minutes at 5° to 100° C. and preferably at 25° to 100° C. in a wash bath which contains 1 to 10 g/kg of a composite washing agent containing builders and 0.05 to 1% relative to the weight of the washing agent, of the brighteners claimed. The liquor ratio can be 1:3 to 1:50. After washing, the textiles are rinsed and dried in the customary manner. The wash bath can contain, as a bleach additive, 0.2 g/l of active chlorine (for example in the form of hypochlorite) or 0.1 to 2 g/l of sodium perborate.

The brighteners according to the invention can also be applied from a rinsing bath with a "carrier". For this purpose the brightener is incorporated in a soft rinsing agent or in another rinsing agent, which contains, as the "carrier", for example, polyvinyl alcohol, starch, copolymers on an acrylic basis or formaldehyde/urea or ethylene-urea or propylene-urea derivatives, in amounts of 0.005 to 5% or more and preferably of 0.2 to 2%, relative to the rinsing agent. When used in amounts of 1 to 100 ml, and preferably of 2 to 25 ml, per litre of rinsing bath, rinsing agents of this type, which contain the brighteners according to the invention, impart brilliant brightening effects to very diverse types of treated textiles.

A further application of the compounds of the invention is for the brightening of paper, either in the pulp mass during paper manufacture or in the size-press, which has been described in British Patent Specification 1,247,934, or preferably in coating compositions. When brighteners of the present invention are employed in such formulations papers brightened with them exhibit a very high degree of whiteness.

The compounds obtained by the process of the present invention are particularly advantageous in that they exhibit not only extremely high whitening ability, but, in addition, in many cases highly desirable water solubilities and also possess excellent white aspects in the solid state.

The following Examples serve to illustrate the invention; parts and percentages are by weight, unless otherwise stated.

EXAMPLE 1

(101)

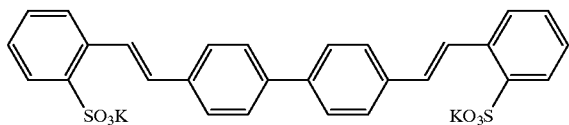

45 g of an aqueous 50% suspension of the sodium salt of 4,4'-bis-(2-sulphostyryl)biphenyl are added to 225 g of deionised water, the pH adjusted to 2–3 by the addition of 60% sulphuric acid and the suspension heated to 60° C. To the well-stirred suspension, 375 g of xylene isomer mixture are added followed by 56.6 g of trioctylamine. By the addition of 7.8 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 60° C., the emulsion allowed to separate and the lower aqueous layer separated off.

The xylene containing layer is mixed with 300 ml of deionised water and the mixture heated to 80° C. Under rapid stirring, the pH is adjusted to 8–8.5 by the addition of 48 g of a 10% aqueous potassium hydroxide solution and stirred for a further hour, whereby the pH is maintained by further addition of the potassium hydroxide solution. Stirring is now ceased to allow phase separation. The lower layer contains the potassium salt of 4,4'-bis-(2-sulphostyryl)-biphenyl in water, whilst the upper layer consists of trioctylamine in xylene. The layers are separated. The organic layer may be used for a further extraction. The aqueous layer is washed with 100 ml of xylene, cooled with stirring to 0° C. and filtered. After drying under vacuum, there are obtained 21.8 g of compound (101).

EXAMPLE 2

(102)

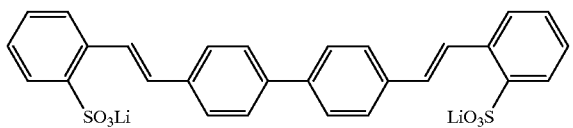

45 g of an aqueous 50% suspension of the sodium salt of 4,4'-bis-(2-sulphostyryl)-biphenyl are added to 225 g of deionised water, the pH adjusted to 2–3 by the addition of 60% sulphuric acid and the suspension heated to 60° C. To the well-stirred suspension, 375 g of xylene isomer mixture are added followed by 56.6 g of trioctylamine. By the addition of 7.8 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 60° C., the emulsion allowed to separate and the lower aqueous layer separated off.

The xylene containing layer is mixed with 300 ml of deionised water and the mixture heated to 60° C. Under rapid stirring, the pH is adjusted to 8–8.5 by the addition of 38.3 g of a 10% aqueous lithium hydroxide solution and stirred for a further hour, whereby the pH is maintained by further addition of the lithium hydroxide solution. Stirring is now ceased to allow phase separation. The lower layer contains the clear, pale yellow solution of the lithium salt of 4,4'-bis-(2-sulphostyryl)-biphenyl in water, whilst the upper layer consists of trioctylamine in xylene. The layers are separated. The organic layer may be used for a further extraction. The aqueous layer is evaporated to dryness under vacuum to yield 26.6 g of compound (102).

EXAMPLE 3

(103)

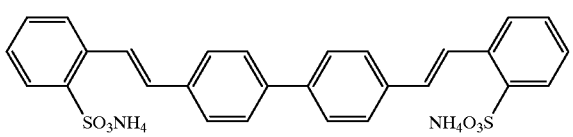

45 g of an aqueous 50% suspension of the sodium salt of 4,4'-bis-(2-sulphostyryl)-biphenyl are added to 225 g of deionised water, the pH adjusted to 2–3 by the addition of 60% sulphuric acid and the suspension heated to 60° C. To the well-stirred suspension, 375 g of xylene isomer mixture are added followed by 56.6 g of trioctylamine. By the addition of 7.8 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 60° C., the emulsion allowed to separate and the lower aqueous layer separated off.

The xylene containing layer is mixed with 300 ml of deionised water and the mixture heated to 60° C. Under rapid stirring, the pH is adjusted to 8–8.5 by the addition of 16 g of a 30% aqueous ammonium hydroxide solution and stirred for a further hour, whereby the pH is maintained by further addition of the ammonium hydroxide solution. Stirring is now ceased to allow phase separation. The lower layer contains the clear solution of the diammonium salt of 4,4'-bis-(2-sulphostyryl)-biphenyl in water, whilst the upper layer consists of trioctylamine in xylene. The layers are separated. The aqueous layer is washed with 100 ml of xylene and, subsequently, evaporated to dryness under vacuum to yield 23.4 g of compound (103).

EXAMPLE 4

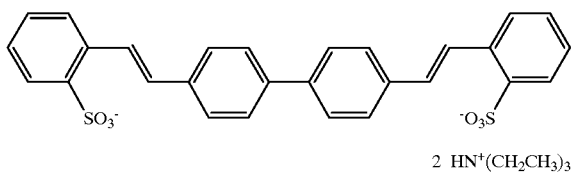

(104)

2 HN⁺(CH₂CH₃)₃

45 g of an aqueous 50% suspension of the sodium salt of 4,4'-bis-(2-sulphostyryl)-biphenyl are added to 225 g of deionised water, the pH adjusted to 2–3 by the addition of 60% sulphuric acid and the suspension heated to 60° C. To the well-stirred suspension, 375 g of xylene isomer mixture are added followed by 56.6 g of trioctylamine. By the addition of 7.8 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 60° C., the emulsion allowed to separate and the lower aqueous layer separated off.

The xylene containing layer is mixed with 300 ml of deionised water and the mixture heated to 60° C. Under rapid stirring, the pH is adjusted to 8–8.5 by the addition of 8.3 g of triethylamine and stirred for a further hour, whereby the pH is maintained by further addition of triethylamine. Stirring is now ceased to allow phase separation. The lower layer is the suspension of the triethylammonium salt of 4,4'-bis-(2-sulphostyryl)-biphenyl in water, whilst the upper layer consists of trioctylamine in xylene. The layers are separated. The aqueous layer is washed with 100 ml of xylene, filtered and dried to yield 26.3 g of compound (104).

EXAMPLE 5

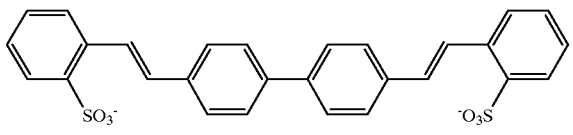

(105)

2 N⁺(CH₂CH₂CH₂CH₃)₄

45 g of an aqueous 50% suspension of the sodium salt of 4,4'-bis-(2-sulphostyryl)-biphenyl are added to 225 g of deionised water, the pH adjusted to 2–3 by the addition of 60% sulphuric acid and the suspension heated to 70° C. To the well-stirred suspension, 400 g of xylene isomer mixture are added followed by 37.7 g of trioctylamine. By the addition of 7.8 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 70° C., the emulsion allowed to separate and the lower aqueous layer separated off and discarded. The xylene containing layer is mixed with 200 ml of deionised water and the mixture heated to 70° C. Under rapid stirring, the pH is adjusted to 8–8.5 by the addition of 36.8 g of a 55% aqueous tetrabutylammonium hydroxide solution stirred for a further hour, whereby the pH is maintained by further addition of the tetrabutylammonium hydroxide solution. Stirring is now ceased to allow phase separation. The lower aqueous layer contains a pale yellow melt of the tetrabutylammonium salt of 4,4'-bis-(2-sulphostyryl)-biphenyl in water, whilst the upper layer consists of trioctylamine in xylene. The layers are separated. The aqueous emulsion is evaporated to dryness under vacuum to yield 36.8 g of compound (105).

EXAMPLE 6

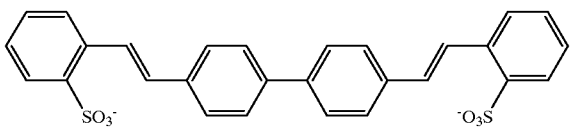

(106)

2 HN⁺(CH₂CH₂OH)₃

63 g of an aqueous 50% suspension of the sodium salt of 4,4'-bis-(2-sulphostyryl)-biphenyl are added to 225 g of deionised water, the pH adjusted to 2–3 by the addition of 60% sulphuric acid and the suspension heated to 60° C. To the well-stirred suspension, 375 g of xylene isomer mixture are added followed by 56.6 g of trioctylamine. By the addition of 11.3 g of 60% sulphuric acid over 1 hour the pH of the mixture is adjusted to 3–4. Stirring is now ceased to allow phase separation, the lower aqueous sodium sulphate containing layer separated off, the organic layer stirred with a further 250 ml of deionised water at 60° C., the emulsion allowed to separate and the lower aqueous layer separated off.

The xylene containing layer is mixed with 250 ml of deionised water and the mixture heated to 80° C. Under rapid stirring, the pH is adjusted to 7–7.2 by the addition of 21 g of triethanolamine and stirred for a further hour, whereby the pH is maintained by further addition of triethanolamine, but ensuring that the ratio of two equivalents of amine for each equivalent of 4,4'-bis-(2-sulphostyryl)-biphenyl is not exceeded. Stirring is now ceased to allow phase separation. The lower layer is the solution of the triethanolammonium salt of 4,4'-bis-(2-sulphostyryl)-biphenyl in water, whilst the upper layer consists of trioctylamine in xylene. The layers are separated. The aqueous layer is washed with 100 ml of xylene and evaporated to dryness under vacuum to yield 26.3 g of compound (106).

EXAMPLE 7

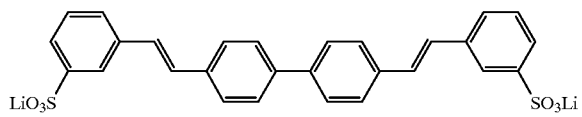

(107)

15 g of the sodium salt of 4,4'-bis-(3-sulphostyryl)-biphenyl are added to 225 g of deionised water, the pH adjusted to 2–3 by the addition of 60% sulphuric acid and the suspension heated to 70° C. To the well-stirred suspension, 400 g of xylene isomer mixture are added followed by 37.7 g of trioctylamine. By the addition of 3 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 70° C., the emulsion allowed to separate and the lower aqueous layer separated off and discarded.

The xylene containing layer is mixed with 300 ml of deionised water and the mixture heated to 70° C. Under rapid stirring, the pH is adjusted to 8–8.5 by the addition of 21 g of a 10% aqueous lithium hydroxide solution and stirred for a further hour, whereby the pH is maintained by further addition of the lithium hydroxide solution. Stirring is now ceased to allow phase separation. The lower layer contains the clear, pale yellow solution of the lithium salt of 4,4'-bis(3-sulphostyryl)-biphenyl in water, whilst the upper layer consists of trioctylamine in xylene. The layers are separated. The organic layer may be used for a further extraction. The aqueous layer is evaporated to dryness under vacuum to yield 14.6 g of compound (107).

EXAMPLE 8

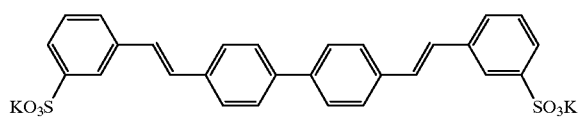

(108)

15 g of the sodium salt of 4,4'-bis-(3-sulphostyryl)-biphenyl with a content of 95% are added to 225 g of deionised water, the pH adjusted to 2–3 by the addition of 60% sulphuric acid and the suspension heated to 70° C. To the well-stirred suspension, 400 g of xylene isomer mixture are added followed by 37.7 g of trioctylamine. By the addition of 3 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 70° C., the emulsion allowed to separate and the lower aqueous layer separated off and discarded.

The xylene containing layer is mixed with 300 ml of deionised water and the mixture heated to 70° C. Under rapid stirring, the pH is adjusted to 8–8.5 by the addition of 14.6 g of a 10% aqueous potassium hydroxide solution and stirred for a further hour, whereby the pH is maintained by further addition of the potassium hydroxide solution. Stirring is now ceased to allow phase separation. The lower layer contains a pale yellow suspension of the potassium salt of 4,4'-bis-(3sulphostyryl)-biphenyl in water, whilst the upper layer consists of trioctylamine in xylene. The layers are separated. The organic layer may be used for a further extraction. The aqueous layer is evaporated to dryness under vacuum to yield 15.2 g of compound (108).

EXAMPLE 9

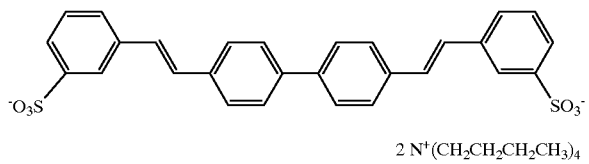

(109)

2 N⁺(CH₂CH₂CH₂CH₃)₄

15 g of the sodium salt of 4,4'-bis-(3-sulphostyryl)-biphenyl with a content of 95% are added to 225 g of deionised water, the pH adjusted to 2–3 by the addition of 60% sulphuric acid and the suspension heated to 70° C. To the well-stirred suspension, 400 g of xylene isomer mixture are added followed by 37.7 g of trioctylamine. By the addition of 3 g of 60% sulphuric acid over 1 hour the pH of the mixture is adjusted to 3–4. Stirring is now ceased to allow phase separation, the lower aqueous sodium sulphate containing layer separated off, the organic layer stirred with a further 300 ml of deionised water at 70° C., the emulsion allowed to separate and the lower aqueous layer separated off and discarded.

The xylene containing layer is mixed with 300 ml of deionised water and the mixture heated to 70° C. Under rapid stirring, the pH is adjusted to 8–8.5 by the addition of 45 g of a 30% aqueous tetrabutylammonium hydroxide solution and stirred for a further hour, whereby the pH is maintained by further addition of the tetrabutylammonium hydroxide solution. Stirring is now ceased to allow phase separation. The lower layer contains a pale yellow melt of the tetrabutylammonium salt of 4,4'-bis-(3-sulphostyryl)-biphenyl in water, whilst the upper layer consists of trioctylamine in xylene. The layers are separated. The organic layer may be used for a further extraction. The aqueous suspension is cooled and filtered to yield, after drying, 19.6 g of compound (109).

EXAMPLE 10

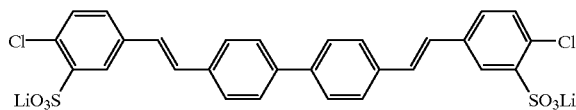

(110)

25 g of the sodium salt of 4,4'-bis-(4-chloro-3-sulphostyryl)-biphenyl are added to 225 g of deionised water, the pH adjusted to 2–3 by the addition of 60% sulphuric acid and the suspension heated to 70° C. To the well-stirred suspension, 300 g of xylene isomer mixture are added followed by 37.7 g of trioctylamine. By the addition of 6 g of 60% sulphuric acid over 1 hour the pH of the mixture is adjusted to 3–4. Stirring is now ceased to allow phase separation, the lower aqueous sodium sulphate containing layer separated off, the organic layer stirred with a further 100 ml of deionised water at 70° C., the emulsion allowed to separate and the lower aqueous layer separated off and discarded.

The xylene containing layer is mixed with 300 ml of deionised water and the mixture heated to 70° C. Under rapid stirring, the pH is adjusted to 8–8.5 by the addition of 33 g of a 10% aqueous lithium hydroxide solution and stirred for a further hour, whereby the pH is maintained by further addition of the lithium hydroxide solution. Stirring is now ceased to allow phase separation. The lower layer contains the clear, pale yellow solution of the lithium salt of 4,4'-bis-(4-chloro-3-sulphostyryl)-biphenyl in water, whilst the upper layer consists of trioctylamine in xylene. The layers are separated. The organic layer may be used for a further extraction. The aqueous layer is evaporated to dryness under vacuum to yield 19 g of compound (110).

EXAMPLE 11

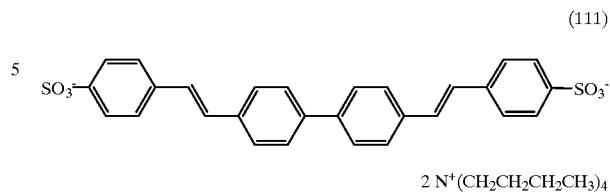

16 g of the sodium salt of 4,4'-bis-(4-sulphostyryl)-biphenyl are added to 225 g of deionised water, the pH adjusted to 2–3 by the addition of 60% sulphuric acid and the suspension heated to 80° C. To the well-stirred suspension, 400 g of xylene isomer mixture are added followed by 37.7 g of trioctylamine. By the addition of 2 g of 60% sulphuric acid over 1 hour the pH of the mixture is adjusted to 3–4. Stirring is now ceased to allow phase separation, the lower aqueous sodium sulphate containing layer separated off, the organic layer stirred with a further 100 ml of deionised water at 80° C., the emulsion allowed to separate and the lower aqueous layer separated off and discarded.

The xylene containing layer is mixed with 300 ml of deionised water and the mixture heated to 80° C. Under rapid stirring, the pH is adjusted to 8–8.5 by the addition of 37 g of a 30% aqueous tetrabutylammonium hydroxide solution and stirred for a further hour, whereby the pH is maintained by further addition of the tetrabulylammonium hydroxide solution. Stirring is now ceased to allow phase separation. The lower layer contains a pale yellow melt of the tetrabutylammonium salt of 4,4'-bis-(4-sulphostyryl)-biphenyl in water, whilst the upper layer consists of trioctylamine in xylene. The layers are separated. The organic layer may be used for a further extraction. The aqueous suspension yields, after drying, 22.6 g of compound (111).

What is claimed is:
1. A process for the preparation of sulphonated distyryl-biphenyl compounds of formula:

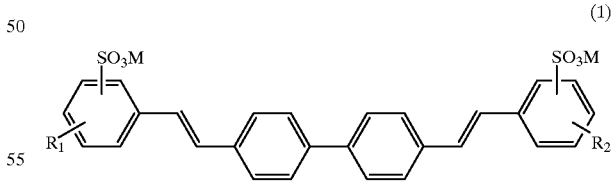

(1)

in which $R_1$ and $R_2$, independently, are hydrogen, $C_1$–$C_5$-alkyl, $C_1$–$C_5$-alkoxy or halogen, and M represents Li, K, an alkaline earth metal, ammonium, a mono-, di- or trialkylammonium or a tetraalkylammonium, all containing 1–4 carbon atoms in each alkyl group; a mono-, di- or tri ($C_2$–$C_4$)alkanolammonium, morpholinium, piperidinium or pyrrolidinium characterized by, firstly, reacting a compound of formula

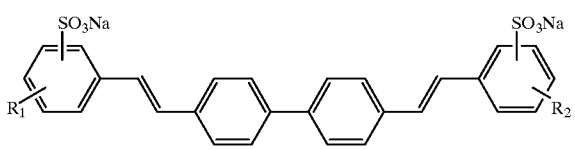
(2)

with a di- or trialkylamine containing 6–12 carbon atoms in each alkyl group, in a two-phase system consisting of strong aqueous mineral acid and a water immiscible organic solvent and, secondly, reacting the resulting lypophilic ammonium salt with LiOH, KOH, an alkaline earth metal hydroxide, ammonia, a mono-, di- or trialkylamine or a tetraalkylammonium hydroxide, all containing 1–4 carbon atoms in each alkyl group; a mono-, di- or tri($C_2$–$C_4$) alkanolamine, morpholine, piperidine or pyrrolidine.

2. A process according to claim 1 in which the strong mineral acid is hydrochloric acid or sulphuric acid.

3. A process according to claim 2 in which the pH of the acid layer in the first reaction step is from 1 to 5.

4. A process according to claim 1 in which the water immiscible organic solvent is a substituted or unsubstituted benzene, alkane or cycloalkane.

5. A process according to claim 1 in which the amine utilised in the first step is a trialkylamine containing 6–10 carbon atoms in each alkyl group.

6. A process according to claim 1 in which the reaction temperature in the first step is between 10 and 90° C.

7. A process according to claim 1 in which the molar ratio of the di- or trialkylamine to that of compound (2) is between 2 and 4.

8. A process according to claim 1 for the preparation of compounds of formula (1), whereby, $R_1$ and $R_2$ both represent hydrogen, $C_1$–$C_3$-alkyl, $C_1$–$C_3$-alkoxy, bromine or chlorine, and M represents Li, K, Mg, Ca or ammonium.

9. A process according to claim 8, whereby $R_1$ and $R_2$ both represent hydrogen and M represents Li, K, Mg, Ca, —$N(R_3)_4$, whereby $R_3$ represents hydrogen or $C_1$–$C_4$-alkyl, or $C_2$–$C_4$-alkanolammonium.

10. A process according to claim 9 for the preparation of compounds of formula

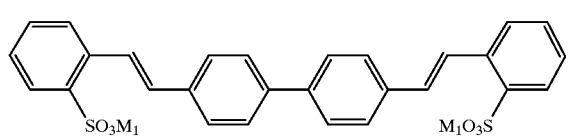
(3)

whereby $M_1$ represents Li, K, —$N(R_3)_4$, where $R_3$ represents hydrogen or $C_1$–$C_4$-alkyl, or $C_2$–$C_4$-alkanolammonium.

11. A process according to claim 9 for the preparation of compounds of formula

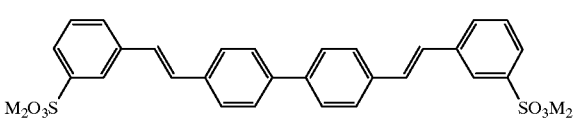
(4)

whereby $M_2$ represents Li, K or —$N(n\text{-}C_4H_9)_4$.

* * * * *